United States Patent
Sonnleitner

(10) Patent No.: US 9,557,260 B2
(45) Date of Patent: Jan. 31, 2017

(54) MEASURING ARRANGEMENT FOR OPTICALLY EVALUATING A CHEMICAL REACTION QUANTITATIVELY

(75) Inventor: Max Sonnleitner, Linz (AT)

(73) Assignee: Greiner Bio-One GmbH, Frickenhausen (DE)

( * ) Notice: Subject to any disclaimer, the term of this patent is extended or adjusted under 35 U.S.C. 154(b) by 83 days.

(21) Appl. No.: 13/993,799

(22) PCT Filed: Dec. 14, 2011

(86) PCT No.: PCT/EP2011/072763
§ 371 (c)(1),
(2), (4) Date: Jul. 11, 2013

(87) PCT Pub. No.: WO2012/080339
PCT Pub. Date: Jun. 21, 2012

(65) Prior Publication Data
US 2013/0294973 A1 Nov. 7, 2013

(30) Foreign Application Priority Data
Dec. 14, 2010 (AT) ................................ A 2066/2010

(51) Int. Cl.
*G01N 21/64* (2006.01)
*G01N 21/77* (2006.01)
(Continued)

(52) U.S. Cl.
CPC ......... *G01N 21/17* (2013.01); *B01L 3/502715* (2013.01); *G01N 21/03* (2013.01);
(Continued)

(58) Field of Classification Search
None
See application file for complete search history.

(56) References Cited

U.S. PATENT DOCUMENTS 6,235,241 B1   5/2001   Catt et al.
7,145,645 B2 *  12/2006   Blumenfeld .......... G06T 1/0007
                                                          356/73
(Continued)

FOREIGN PATENT DOCUMENTS

AT          504 919         9/2008
CA         2 468 014        12/2004
(Continued)

OTHER PUBLICATIONS

International Search Report of PCT/EP2011/072763, Mar. 22, 2012.
International Preliminary Report on Patentability of PCT/EP2011/072763, Jun. 14, 2013.

*Primary Examiner* — Neil N Turk
(74) *Attorney, Agent, or Firm* — Collard & Roe, P.C.

(57) ABSTRACT

The invention relates to a measuring arrangement for optically evaluating a chemical reaction quantitatively, comprising a sample carrier having a carrier layer and a sample layer having an analysis side and a light outlet side opposite the analysis side, and comprising a photosensitive sensor having a plurality of photodetectors on a carrying body and having a transparent surface layer arranged over the photodetectors. A plurality of test sections are arranged on the analysis side at a distance from each other in a longitudinal direction of the sample layer. The analysis side is arranged on the carrier layer in such a way that the test sections face a volume of a microfluidic system. The sample carrier is detachably arranged in an accommodating device, so that the light outlet side faces the photosensitive sensor and the test sections are arranged over the photodetectors. Furthermore, the distance between the test sections and the photodetectors is less than 700 µm.

14 Claims, 11 Drawing Sheets

(51) Int. Cl.
*G01N 21/17* (2006.01)
*G01N 21/03* (2006.01)
*G01N 21/76* (2006.01)
*B01L 3/00* (2006.01)
*G01N 21/65* (2006.01)
*G01N 21/78* (2006.01)
*G01N 21/82* (2006.01)

(52) U.S. Cl.
CPC ....... *G01N 21/648* (2013.01); *G01N 21/6454* (2013.01); *G01N 21/76* (2013.01); *G01N 21/77* (2013.01); *G01N 21/7703* (2013.01); *B01L 2200/16* (2013.01); *B01L 2300/021* (2013.01); *B01L 2300/022* (2013.01); *B01L 2300/049* (2013.01); *B01L 2300/0654* (2013.01); *B01L 2300/0816* (2013.01); *B01L 2400/0481* (2013.01); *G01N 21/78* (2013.01); *G01N 21/82* (2013.01); *G01N 2021/0325* (2013.01); *G01N 2021/0346* (2013.01); *G01N 2021/7783* (2013.01); *G01N 2021/7786* (2013.01)

(56) References Cited

U.S. PATENT DOCUMENTS

| | | |
|---|---|---|
| 8,454,894 B2 | 6/2013 | Padinger et al. |
| 2002/0123059 A1 | 9/2002 | Ho |
| 2003/0064005 A1 | 4/2003 | Sasaki et al. |
| 2003/0157581 A1 | 8/2003 | Grill et al. |
| 2003/0235924 A1 | 12/2003 | Adams et al. |
| 2005/0196779 A1* | 9/2005 | Ho et al. ............... 435/6 |
| 2006/0063160 A1 | 3/2006 | West et al. |
| 2009/0111207 A1* | 4/2009 | Choumane et al. ........... 438/70 |
| 2011/0136248 A1 | 6/2011 | Sonnleitner |
| 2011/0201099 A1* | 8/2011 | Anderson et al. ......... 435/287.2 |

FOREIGN PATENT DOCUMENTS

| | | |
|---|---|---|
| DE | 196 11 347 | 9/1997 |
| DE | 10 2004 027 130 | 1/2005 |
| EP | 0 283 285 | 9/1988 |
| EP | 1 672 356 | 6/2006 |
| WO | WO 02/08458 | 1/2002 |
| WO | WO 2006/026796 | 3/2006 |
| WO | WO 2007/054710 | 5/2007 |
| WO | WO 2010/055308 | 5/2010 |

* cited by examiner

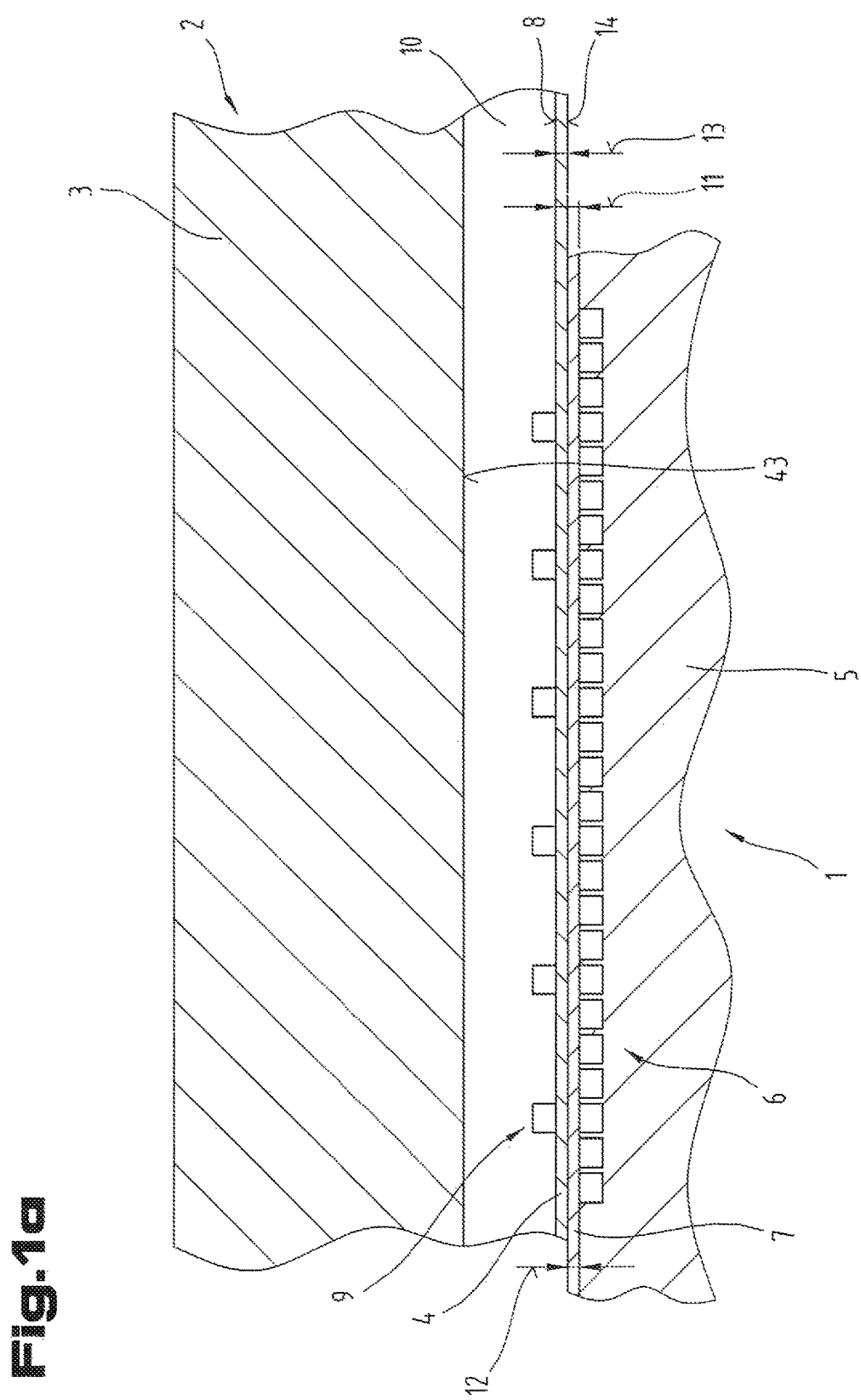

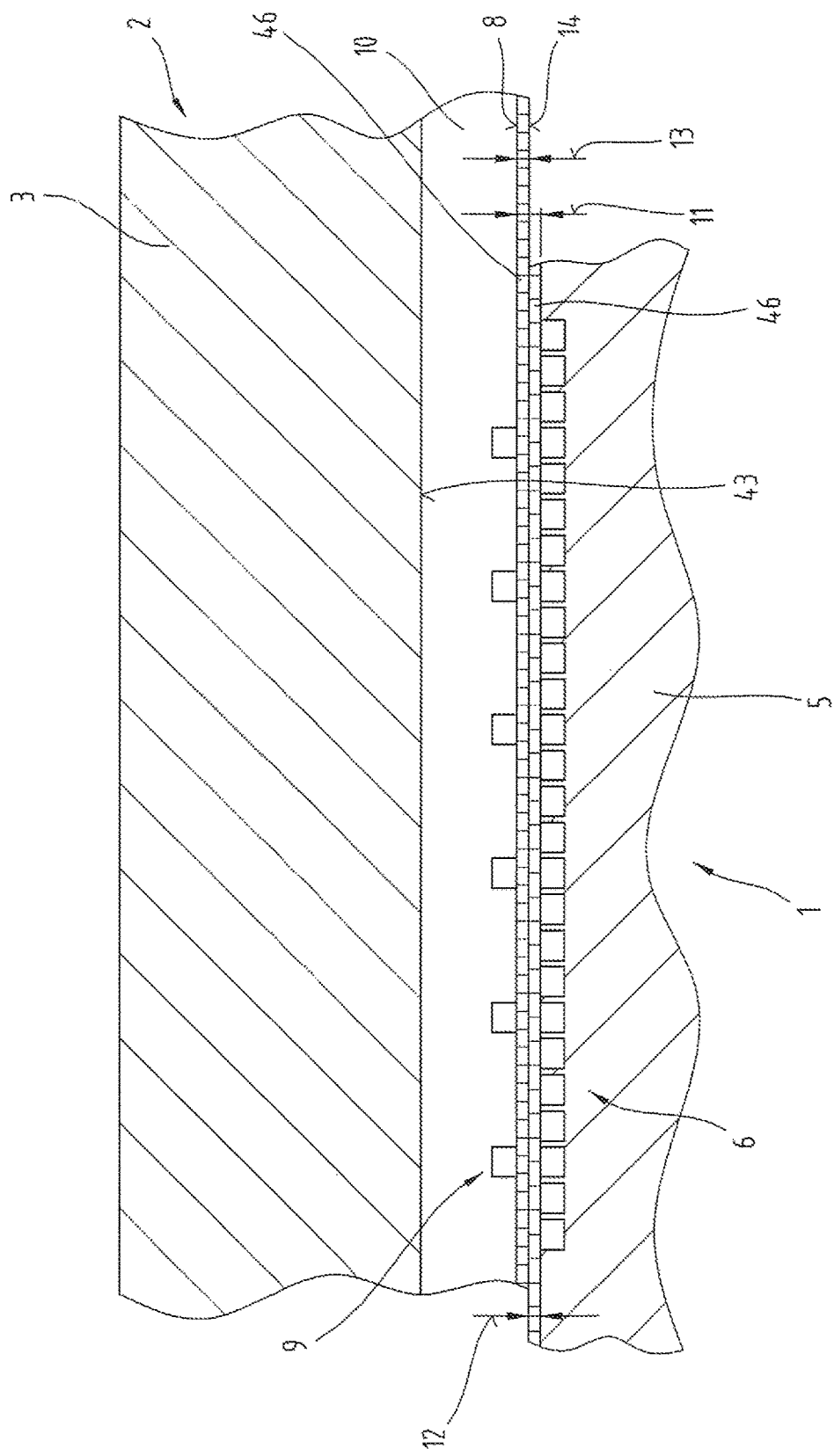

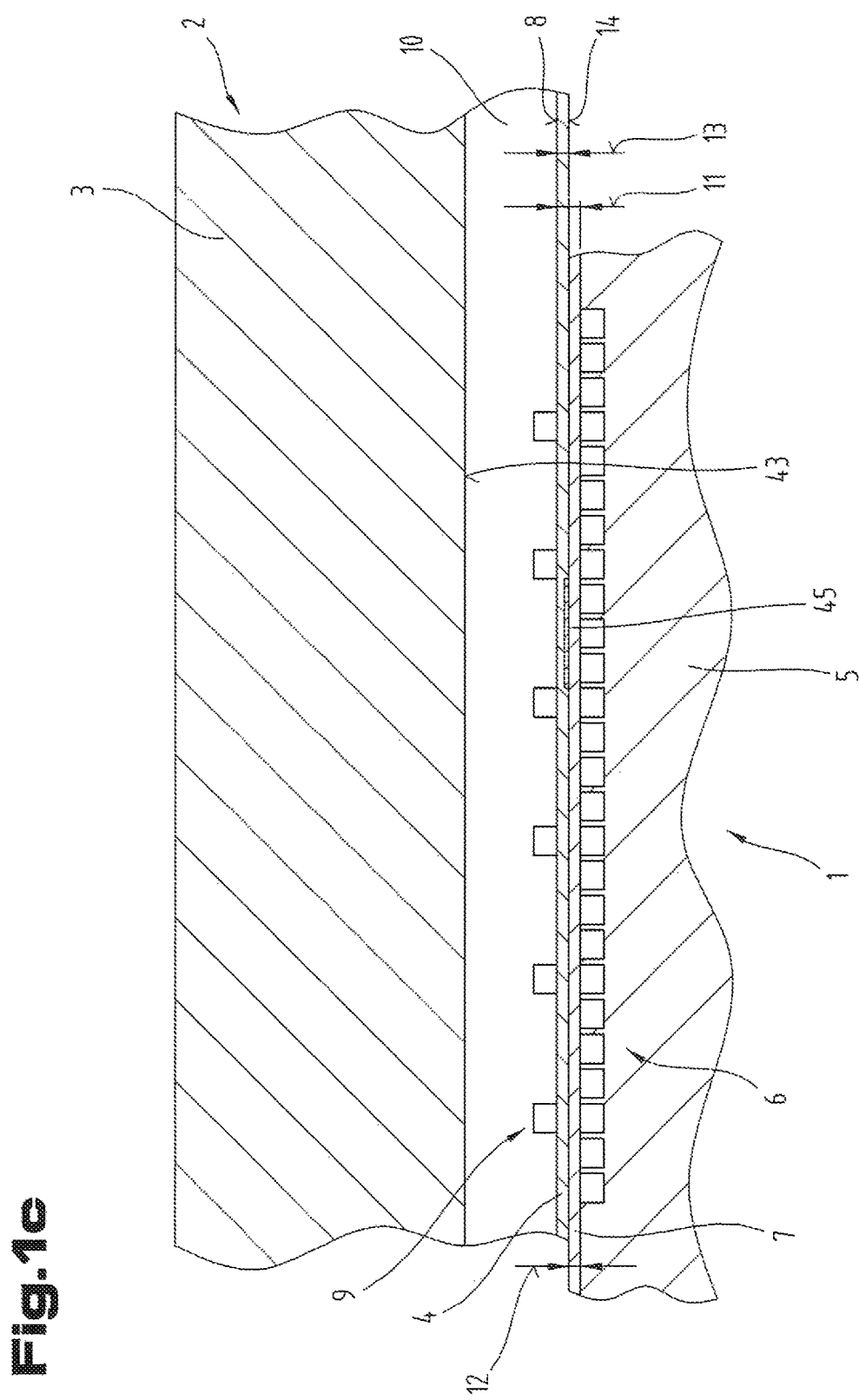

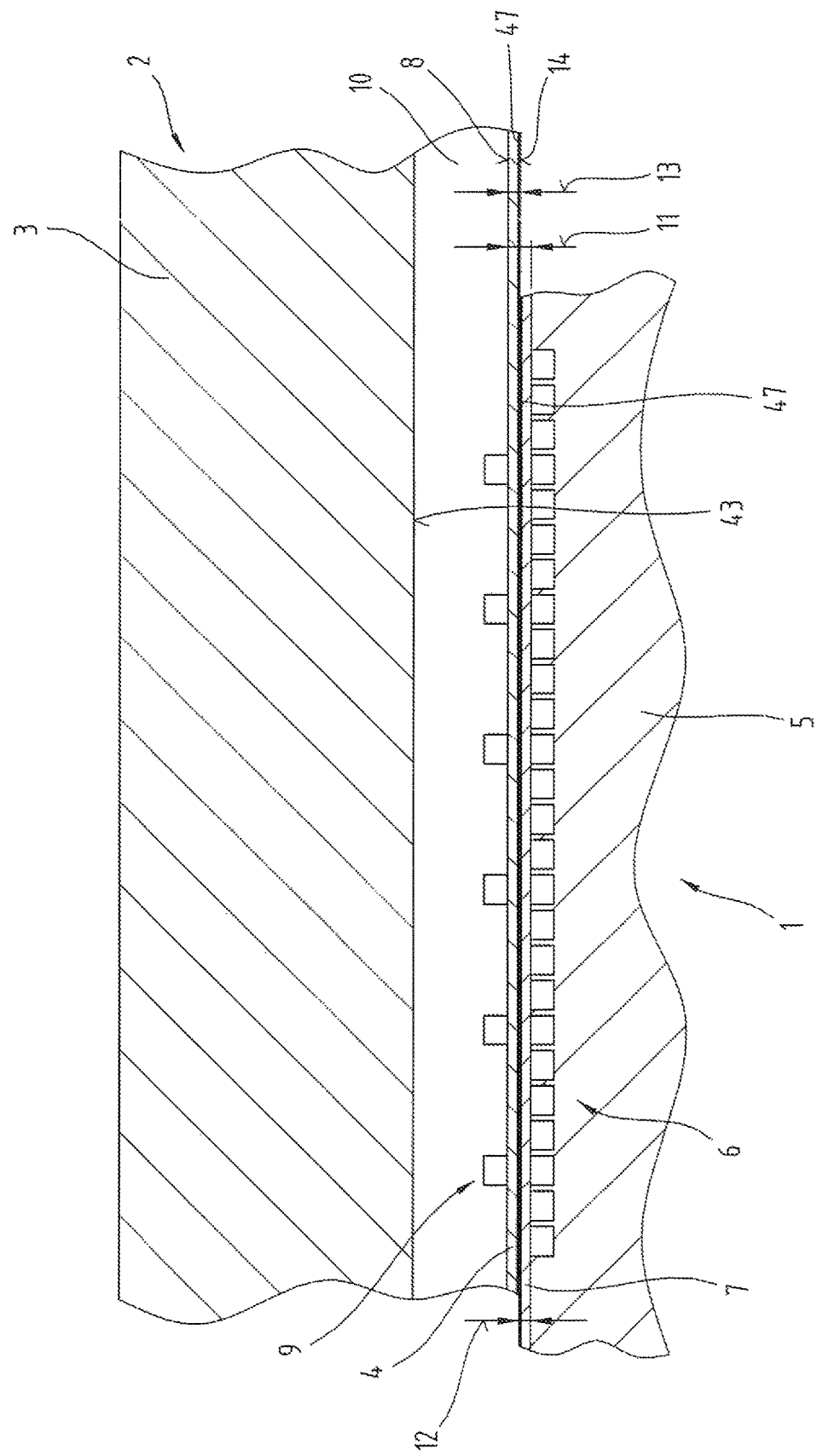

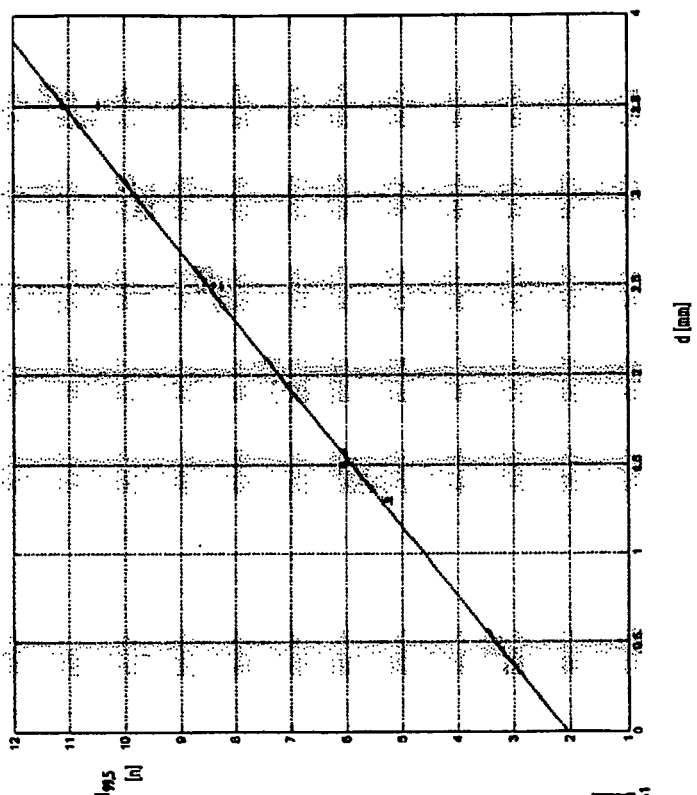
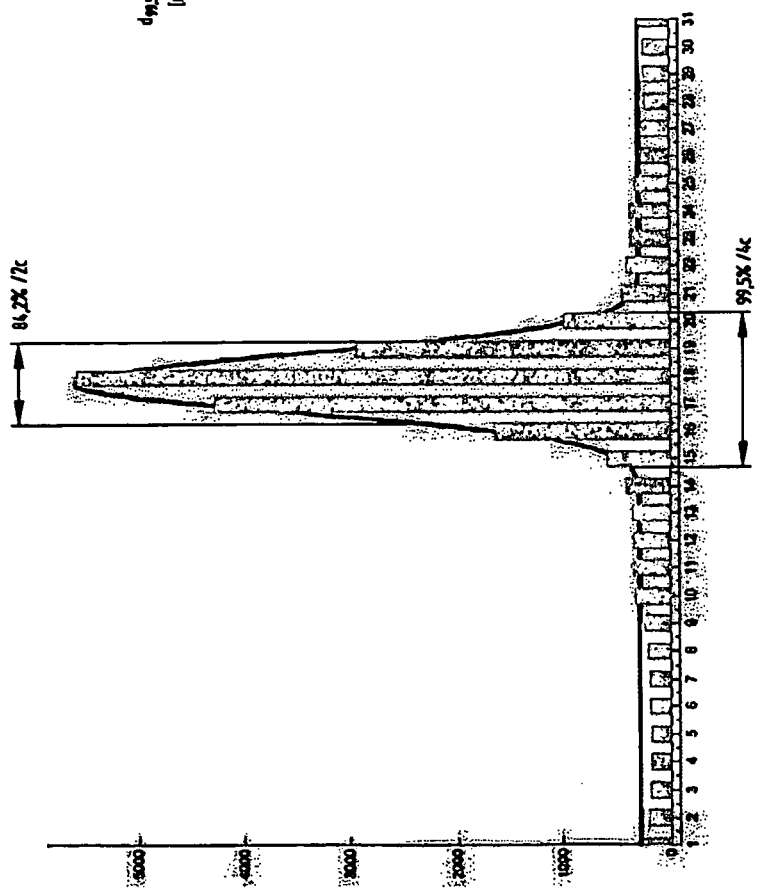
Fig.2b
Fig.2a

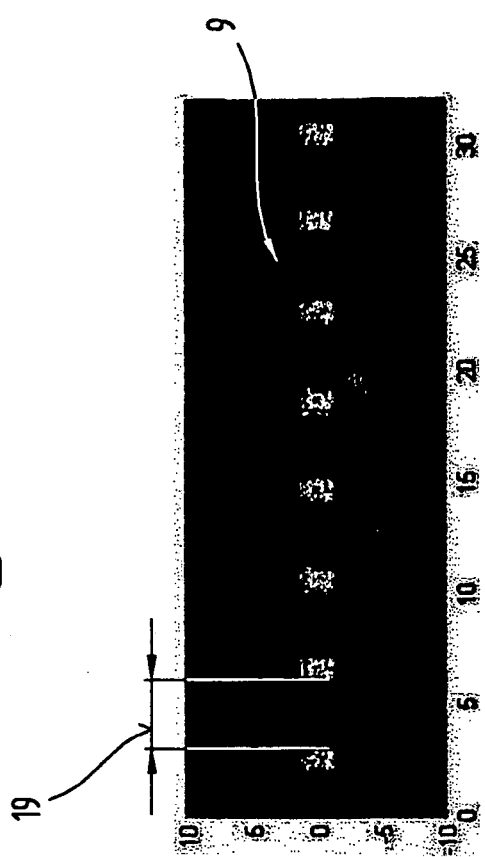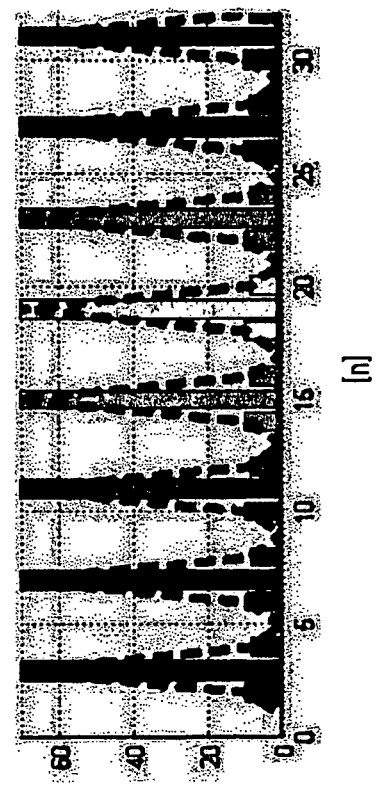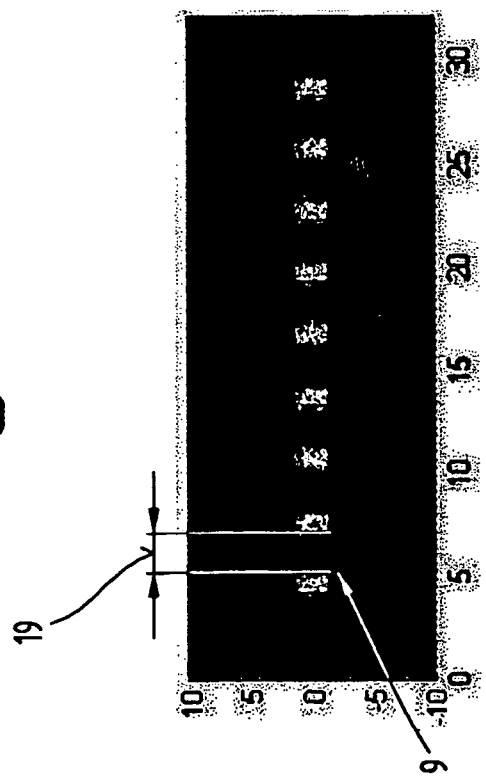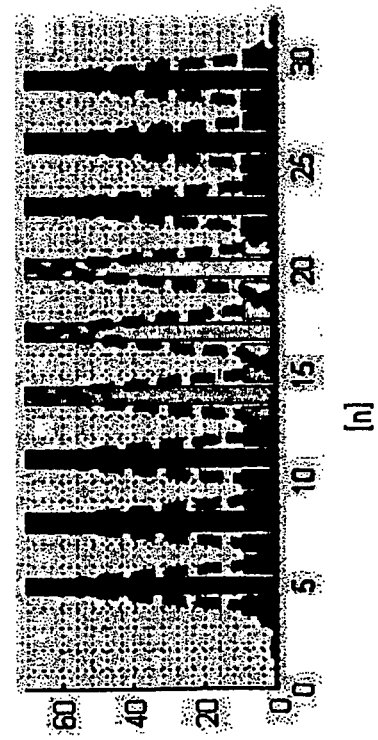

MEASURING ARRANGEMENT FOR OPTICALLY EVALUATING A CHEMICAL REACTION QUANTITATIVELY

CROSS REFERENCE TO RELATED APPLICATIONS

This application is the National Stage of PCT/EP2011/072763 filed on Dec. 14, 2011, which claims priority under 35 U.S.C. §119 of Austrian Application No. A 2066/2010 filed on Dec. 14, 2010, the disclosure of which is incorporated by reference. The international application under PCT article 21(2) was not published in English.

The invention relates to a measuring arrangement for optically evaluating a chemical reaction quantitatively.

In a chemical reaction it is possible for the result of the reaction to be a color change or a change in transmission, it is also possible that there is release of electromagnetic radiation from the chemical reaction. In the measuring method used here a sample to be analyzed, which is mostly in liquid form, is moved in a microfluidic system past at least one test section, where with the presence of an analyte in the sample and a suitably corresponding reagent in the test section a chemical reaction takes place which is expressed in a change in the transmittance of the test section or in the release of electromagnetic radiation from the test section.

To evaluate the result of the reaction, which is directly connected to the quantitative presence of analyte in the sample, it is known to capture the test section with a photosensitive sensor and evaluate the time-dependent behavior of the detected, optical signal. As the optical effects to be evaluated are often only very small, it is particularly important, that the optical detector has a high degree of sensitivity, to achieve the greatest possible signal-to-noise ratio (SNR), which produces in turn the lowest possible detection threshold (LOD). In known evaluation devices a photodiode array is arranged ahead of the test section, wherein a test section is captured by a plurality of photodetectors, for example 5 to 7 photodetectors. However, this has the disadvantage that the electromagnetic radiation incident on each individual photodetector is reduced and thus the incidental or detected signal is often only slightly greater than the unavoidable inherent noise of the photodetector, whereby a very low SNR is obtained. To achieve the highest possible resolution and the same time a very low detection threshold it is a disadvantage if the signal of a test section is split between several photodetectors. Furthermore, it is also a disadvantage if the optical reaction, a change in the transmittance or luminescence, occurs because of dispersion effects on adjacent photodetectors not originally assigned to the relevant test section.

For example document WO 02/08458 A1 discloses a method for the high-sensitivity resolution detection of electromagnetic radiation. In addition it discloses arranging an imaging, photoelectric surface sensor at the smallest possible distance from the surface of the biochip, so that electromagnetic radiation which comes from an area of the surface of the biochip can be assigned in a clear way to a specific area of the surface sensor. In this way it is achieved that a defined area of the biosensor is assigned to each photoselective element of the surface sensor and thus the corresponding element does not need to be shielded from scattered light from adjacent areas of the surface sensor. By evaluating the optical reaction signal this enables a clear spatial allocation of the substance to a field element of the biochip. By means of the immediate closeness of the signal generation and detection it is possible to avoid having display optics. In a preferred embodiment the biochip is applied directly onto the sensor surface. In a further embodiment a spacer is arranged between the surface sensor and the biochip and a reaction chamber is defined thereby. For the detection typically surface sensors are used with more than 10,000 pixel, wherein by means of direct contact or a very small distance between the surface sensor and surface of the biochip, there is a kind of contact light exposure. By means of the direct arrangement on the sensor surface or the spaced apart arrangement for forming a reaction chamber, the surface sensor gets contaminated by sample material, so that the surface sensor or the entire detection system, into which the surface sensor is integrated, has to be washed and dried after the measurement in order to be used again. If between the surface sensor and the biochip there is a reaction chamber a spatial resolution of 20 µm or more is achieved. With direct contact between the surface sensor and biochip the resolution corresponds to the pixel size of the sensor. The distance between the surface of the biochip and the surface sensor is selected such that each pixel element of the sensor essentially only receives light from immediately opposite areas of the biochip. The distance between the surface sensor and biochip should therefore not be essentially greater than the edge length of a pixel of the surface sensor.

From document US 2003/0235924 A1 a spectroscopy device is known in which the optoelectronic and microfluidic system are integrated. This device also does not have a lens system between the microfluidic system and the detector system. The sample mounting device is configured such that the sample to be analyzed is arranged at a distance of up to 50 times the pixel dimension. The highest resolution of the detector system is determined by the pixel size and is thereby less than 10 µm. For example the active area of a pixel can be 3 µm×3 µm. The microfluidic system can for example be arranged directly on the detector system, with or without an intermediate layer, also the microfluidic system can be arranged in the immediate vicinity.

A microarray measuring system with a microfluidic system is also known from US 2006/0063160 A1. Here too the image is detected by a high pixel CCD-array.

Document WO 2007/054710 A2 shows a transmitted light measuring device based on organic semiconductor elements. From an OLED light is emitted into a channel, which light penetrates the channel and is detected by a photodiode arranged opposite the OLED.

Furthermore, from US 2002/0123059 A1 a detection system is also known which comprises a disposable biochip, which comprises an arrangement of closed test sections and a microfluidic system.

The objective of the invention is thus to create a measuring arrangement, in which the signal-to-noise ratio of the reaction detection is improved in relation to the prior art and thus a lower detection minimum is achieved.

The objective of the invention is achieved in that in a measuring arrangement with a sample carrier and a photosensitive sensor the distance between the test sections arranged on a sample layer of the sample carrier and the photodetectors is less than 700 µm. The sample carrier has a carrier layer and a sample layer, wherein the carrier layer also has a delivery section, which is connected via a microfluidic system to a reservoir. The sample layer has an analysis side and opposite the latter a light outlet side, wherein on the analysis side spaced apart from one another in a longitudinal direction of the sample layer a plurality of test sections are arranged and wherein furthermore the sample layer with the analysis side is arranged on the carrier layer such that the test sections are turned to face a volume of the microfluidic system. This arrangement has the advantage that the test sections come into contact with the sample material transported in the microfluidic system, in particular a liquid sample material, and thus the chemical reaction can take place.

The sample material is thereby applied to the delivery section, transported via the microfluidic system past the test sections to a reservoir. The reservoir is in particular large enough to hold the total amount of samples or reagents necessary for performing the measurement, in particular hold them securely, so that it is essentially impossible for the operator to come into contact with the sample material.

The photosensitive sensor comprises a plurality of photodetectors on a support body, wherein a transparent cover layer is arranged over the photodetectors. The transparent cover layer is configured such that the individual photodetectors are protected reliably, the layer for achieving the configuration according to the invention is sufficiently thin however but is still sufficiently resistant to solvents and detergents, as in particular the photosensitive sensor has to be cleaned cyclically in order to reliably prevent the operating staff being contaminated with sample residue. The cover layer can be for example in the form of an epoxy resin.

As the sample carrier can be arranged removably in a mounting device of the sensor, so that the light outlet side faces the photosensitive sensor and the test sections are arranged over the photodetectors, the sample carrier, in particular a disposable sample carrier, can be inserted easily into the measuring arrangement, the measurement of the chemical reaction can be performed and the sample carrier can then be removed from the measuring arrangement and disposed of.

According to a further development the thickness of the cover layer is less than 500 µm. A reduction in the thickness of cover layer to this value has the advantage over photosensitive sensors known from the prior art, in which the thickness is mostly greater than 1000 µm, that a clear approach of the test section to the photosensitive sensor is possible without impairing the mechanical protection of the individual photodetectors or the electrical contact of the photodetectors.

To address the problem according to the invention it is also an advantage if the thickness of the sample layer is less than 200 µm, as the distance between the test section and the photosensitive sensor is reduced in this way, which leads directly to more light on the photodetector and a lower dispersion width. The sample layer is made for example of polystyrene or COC (Cyclic Olefin Copolymers).

On the basis of investigations which led to the measuring arrangement according to the invention it has proved to be an advantage if the photosensitive sensor has at least 32 photodetectors, as in this way for standard laboratory sample carriers (1"/3") an optimum SNR and very low detection threshold are achieved, wherein the photosensitive sensor can be formed by a modified standard component. The use of standard components has the particular advantage that the costs of the measuring arrangement can be kept low and in this way there is a high degree of acceptance by users. In this configuration it is an advantage if a test section also has a dimension of in the region of (0.5-1.5 mm)×(2-4 mm), a dimension of 1×2 mm being preferred.

To address the problem according to the invention it is also an advantage if the distance between two adjacent photodetectors is less than 150 µm, as in this way the proportion of unused area of the photosensitive sensor is reduced. In a transmission measurement or emission measurement as far as possible a continuous, photosensitive section should be available so as not to lose light for the evaluation which does not fall on an area occupied by the photodetector. The smaller the distance between the photodetectors, the more light falls on the latter and therefore also the detected intensity and thereby the SNR are increased.

To address the problem of the invention it is an advantage if as much light as possible falls from the direction of a test section onto a photosensitive sensor assigned to the respective test section. On the basis of the given intensity distribution, which will mostly be a Gaussian distribution, it is however an advantage according to one development if at least 99.5% of the electromagnetic radiation incident on the photosensitive sensor is distributed on a maximum of three photodetectors. It is ensured in this way that the majority of the light intensity falls on an individual sensor and only a very small peripheral amount falls on the two adjacent photodetectors.

To increase the measurements that can be performed simultaneously it is an advantage if according to one development the photosensitive sensor has at least two rows of photodetectors arranged spaced apart next to one another. In a sample carrier with a suitably configured microfluidic system thus at the same time twice the number of reaction measurements can be carried out which brings about an increased throughput. Preferably, in particular a row or strip-like configuration of the photodetectors is preferred, as it is an advantage for the microfluidic system, if a channel is formed which is as straight as possible and thus the test sections and thereby also the photodetectors are arranged in the longitudinal direction of the channel.

Accordingly to one development the channel of microfluidic system arranged over the photodetector has a length of 30-50 mm, a width of 1-4 mm and a height of 10-200 µm, which on the one hand has the advantage that said channel or said microfluidic system can be produced cost-effectively by injection molding the carrier layer. On the other hand said channel has a very small volume, so that the use of sample chemicals or sample material is minimized, which is an advantage for the efficiency and acceptance of the method. Preferably, the channel has a length of 40 mm, a width of 2 mm and a height of 100 µm.

A development is also advantageous in which when delivering a sample to the delivery section in the channel a pressure gradient is formed with a resulting capillary force in the direction of the reservoir, as it is ensured in this way that there is an automatic throughput of the sample through the channel or the microfluidic system, i.e. in particular no means are necessary for generating a pressure difference or a flow movement. In particular, this is a so-called convection-driven hybridization, in which convection gradients are formed in the channel, which in addition to guiding the sample through the channel also ensure the guiding of the sample material to the test sections.

According to one development the cover layer of the photodetector has a transparency maximum in the spectral range of 400-600 nm. The cover layer is preferably formed by an epoxy resin, which was influenced by additives, in particular by known dyes for plastics, in its spectral properties such that it has a transparency maximum only in the spectral range preferred for chemiluminescence-measurements. In this way it is achieved that light not originating from a chemiluminescent reaction does not pass through the cover layer or only passes it in a much reduced manner and thus does not disrupt or only slightly influences the measurement result. In a further development the transparency maximum can also be placed by additives in a different wavelength range, so as to be optimized for transmission measurements for example.

In case of inaccuracies in the production of the sample carrier, in particular a slight deviation in position, in particular when printing the test sections, and slight deviations in the arrangement of the sample carrier in the mounting device, it may be that a test section is not arranged exactly over a corresponding photodetector. If according to one development the center-to-center distance between two adjacent test sections is greater than or equal to 3-x the center-to-center distance of the photodetectors, this has the advantage that even if the alignment is inexact this does not influence the result of the detection, in particular there is essentially no negative effect on the signal-to-noise ratio and thus the measurement sensitivity is not impaired. As furthermore the light coming from the test section has an essentially Gaussian intensity distribution, in this way, even if the positioning is imprecise, a conclusion can be drawn about the intensity maximum of the incidental light, for example by means of interpolation in consideration of the Gaussian distribution, whereby more signal portions flow into the evaluation which is an advantage for the signal-to-noise ratio. In particular, in the configuration of the measuring arrangement according to the invention and at the spacing of 3 mm according to the claims there is a positioning precision of +/−0.45 mm, at a distance of 4 mm the positioning precision would be +/−0.9 mm. In this way the measuring arrangement according to the invention is particularly suitable for daily use, as possible positioning errors can be largely eliminated by the development according to the invention.

The solution to the problem according to the invention can also be achieved in that more light falls on the photosensitive sensor, so that according to one development the boundary surface of the channel arranged opposite the photosensitive sensor is configured to be optically reflective. This reflection can be achieved for example by a reflective surface of the boundary surface. However, it is also possible to have a layer structure so that there is a refractive index jump and incidental light is deflected back to the photosensitive sensor. For transmission measurements for example it is possible to make the side delimiting walls of the channel reflective in order to ensure in this way light deflection to the sample material and avoid scattered light falling on the photosensitive sensor. However, it is also possible for the carrier layer to be configured to be optically reflective, for example in that the latter is made from a white material, which in contrast to a transparent material reflects back most of the incidental light.

A development in which the channel has a concave cross section relative to the photosensitive sensor has the advantage that a concave cross section functions as a converging lens or converging mirror and thus light, which leaves the test section in a direction opposite the photosensitive sensor, is thrown back and in particular is focused on the photosensitive sensor. The concave surface can therefore preferably be reflective or have a refractive index coating. However, it is also possible that the channel in longitudinal direction has a concave profile in some sections. Both possible configurations have the advantage that more scattered light is directed to the photosensitive sensor and is thus available for the detection.

A further way of increasing the light intensity on the photosensitive sensor is that the light outlet side has at least in sections a light deflecting structure, which for example can be configured as an embossed structure with a sawtooth or triangular profile. Said light deflecting structure prevents light which has passed the test section or comes from the latter being scattered into adjacent sections and thus being lost for the intensity measurement at the assigned photodetector, in that such light beams are directed back in the direction of the assigned photodetector. An embossed structure also has the advantage that at the transition of the sample carrier, in particular of the sample layer, to the unavoidable air gap between the sample carrier and the photosensitive sensor, because of the different refractive index there may be total reflection in the cover layer of the photosensitive sensor and thus parallel to the photodetectors. By means of the embossed structure the angular relationships at the transition from the sample carrier to the sensor can be influenced positively to reduce the risk of total reflection as far as possible.

According to one development the sample layer is configured as a fiber-optic panel. Such a fiber-optic panel is formed in that a plurality of optic fibers are arranged closely next to one another, wherein the end faces of the optic fibers form the analysis side or light outlet side. The intermediate space between the individual fibers can be formed for example by a transparent setting resin. In this way light which comes from the test section or passes the latter is taken up by the optic fibers and directed specifically to the photodetector, whereby in this way it is also possible to detect and direct scattered light. It is also possible that the ends of the optic fibers are in the form of microoptics, in order in this way to achieve an improved converging effect or improved focusing and thereby an increase in the light intensity directed to the photodetector. At the transition from the air gap to the cover layer total reflection may occur in the cover layer, whereby the incidental light for the detection is lost. Therefore, the cover layer can also be configured as such a fiber panel and ensures a specific deflection of incidental light to the photodetectors.

At the transition from the sample carrier to the photosensitive sensor mostly there is a small air gap, wherein from the transition from the sample carrier to the air gap and from the air gap to the photosensitive sensor, there is a jump in the refractive index, whereby if necessary there is total reflection and thereby a loss of the reflected light beams. According to a further development the sample layer has at least in some sections a refractive index stepped profile in the direction of is thickness, wherein said profile is configured such that the refractive index difference between the light outlet side of the sample layer and the air gap is as small as possible so as to lose as little light as possible by total reflection at this boundary surface and to deflect as much light as possible in the direction of the photosensitive sensor. The stepped index profile in the direction of the thickness of the sample layer is configured in a similar manner, i.e. has a plurality of smaller refractive index differences so as to deflect as much light as possible from the test section to the light outlet side. The refractive index stepped profile can be formed for example in that the sample layer is formed by a plurality of layers arranged tightly next to one another of a material with a specific refractive index, which changes slightly from layer to layer. Furthermore, it is possible that a plurality of layers, each with a specific refractive index, are applied from the vapor phase in order to form the stepped profile in this way.

In a further development in the same direction the sample layer has a refractive index gradient profile in the direction of its thickness at least in some sections. A gradient profile provides a stepless adjustment of the refractive index of the sample layer to the air in the air gap and thereby provides a particularly optimum deflection of light from the test section to the photosensitive sensor. A gradient profile is preferably formed from the vapor phase so that there is a continuous path of the refractive index. As the cost of producing a specific refractive index profile is quite high, such a refractive index profile is arranged at least in the section of the sample length in which the applied test sections are also located.

A further way of preventing a jump in the refractive index is that an immersion layer is applied onto the light outlet side of the sample layer or onto the cover layer of the photosensitive sensor, whereby by means of this layer air is forced out of the gap between the sample layer and sensor and in this way a jump in the refractive index to the air or from the air to the cover layer is prevented. The immersion layer can be applied for example in the form of an immersion oil, as known from microscopy. It is also possible for example that a depot is provided on the light outlet side, which is activated when placing the sample carrier into the mounting device and thereby applies the immersion material on the light outlet side. Said development has the advantage that no additional operational steps are necessary which is particularly important for use in the field or for single use.

When performing the sample analysis it is mostly necessary to document the measurement result. Therefore, it is an advantage if an identity or identification mark is provided on the sample carrier, as in this way there can be a direct allocation of the read signal path of the individual test sections to a measurement protocol. Furthermore, different sample carriers can be used with different test sections, so that for example an identifier or configuration data of the test sections can also be saved in the identification mark. The feature can preferably be read without contact and can be formed for example by a 1D or 2D code, however, it is also possible to have an RFID mark.

To modularize the measuring arrangement according to the invention a development is possible according to which energy directing sensors are applied to the analysis side and/or the side of the carrier layer facing the analysis side, which by means of ultrasound welding enable the sample layer to be joined to the sample carrier. In this way it is possible to produce the carrier layer and sample layer separately from one another, in particular provide a universal carrier layer, which is joined to a plurality of specifically designed sample layers, in particular with specific test sections, to form the measuring arrangement according to the invention.

As the radiation coming from the test section is largely undirected, a development for a fluorescence measurement is advantageous in which the sample layer and/or the carrier layer are configured as optical polarizers. If the light incidental to the test section is polarized, by means of a polarization direction of the sample layer orthogonal thereto the incidental light can be faded out so that only light coming from the test section is incidental to the photodetector. A polarization arrangement consists of two polarizing components, which are known by the terms polarizer and analyzer. According to a development of the invention the sample layer forms the analyzer. The polarizer can be formed by the carrier layer, it is also possible that a lighting device is provided which comprises a polarizer, by means of which the individual test sections are illuminated. By means of the extensive masking of the incidental excitation light even very small reaction products can be read clearly which in turn reduces the LOD.

The objective of the invention is also achieved by a measuring device for the optical evaluation of a chemical reaction, which measuring device comprises a measuring arrangement according to the invention, wherein the sensor is arranged in a base body and a cover cap can be pivoted between a measurement position and a supply and removal position. As the light intensities of both the chemiluminescence measurements and transmission measurements are very low it is important that the cover cap in the measuring position seals the sample carrier and a section of the base body from the environment to be impermeable to light, as it is thus ensured that no external light can influence the measurement. This seal can be formed for example by a groove-like contact section between the base body and cover cap. Furthermore, an elastic seal surrounding the area to be sealed off can be provided, which in the measuring position is pushed by the cover cap against the base body and thereby ensures a light impermeable seal.

In transmission measurements the weakening of light passing the test section caused by the chemical reaction is determined so that according to one development a lighting device is provided in the cover cap which deflects its light in the direction of the test sections. The lighting device can be formed for example by a luminescence emitter and/or an LED arrangement. It is also an advantage if the position of the light output can be influenced specifically along the test section. If for example a specific light pattern is emitted, it is possible to perform a calibration of the photosensitive sensor, whereby impurities can be determined by the thus created disruption of the expected brightness distribution. A configuration with four light-emitting diodes is preferred which are arranged such that entire longitudinal extension of the photosensitive sensor can be illuminated.

To extend the area of application of the measuring device according to the invention or adapt it to different test sections it is an advantage if the lighting device can emit selectively controllable light in a plurality of wavelengths. In addition, the lighting device can comprise a plurality of light sources which each emit light in a different spectral range, or the light source can be configured to be adjustable and thus emit light in a specific spectral range. It is also an advantage if the lighting device is configured such that light can be emitted along the longitudinal extension of the photosensitive sensor to a plurality of positions, for example in that a plurality of discrete lighting sources are provided. In this way a specific lighting pattern or a specific intensity distribution can be created on the photodetector.

Furthermore, for fluorescence measurements a development is advantageous in which the lighting device comprises a polarizer, wherein preferably the sample layer is configured as an analyzer. The polarization direction of the polarizer and the analyzer are aligned normally to one another, which has the advantage that the polarized exciting light of the lighting source is not detected by the photodetectors, the unpolarized fluorescent light passes through the analyzer however and is thus detected by the photodetectors.

As to perform the measurement the emission of different reagents can be necessary, according to one development an output device for reagents is arranged in the cover cap or in the base body. In said output device one or more reagents can be arranged in containers which can be applied jointly, selectively or before the sample to be analyzed onto the sample carrier and are used during the measurement.

According to one development the output device comprises an activating element and a depot for reagents, wherein the depot is preferably designed to be connectable. The activating element can be formed for example by a push button or a perforation device and thereby releases an optional amount of the content of the depot or the provided content. A connectable depot has the advantage that in this way a disposable system can be formed, in which the sample carrier and the depot are selected for performing the measurement and are disposed of afterwards. This is an advantage in particular for application safety, as the operator can make sure that the right reagents are used and does not need, as was previously necessary, to handle bulky containers of the required reagents which was always associated with a risk of contamination. The connecting device can be formed for example by a membrane-needle-combination, whereby the membrane tightly seals a container of the sample delivery device and on insertion is pierced by a hollow needle or spike in order in this way to provide the sample chemical provided in the container. In particular, the sample delivery device can be configured such that multiple connections are possible. A membrane would close access automatically after the removal of the needle. However, it is possible for a spring-tensioned closing cap to be pressed through a removal spike and thus enable access to the sample chemical.

In a further development the depot can be formed by a blister, wherein reagents can be provided in individually sealed chambers. The chambers are provided with a seal which is broken by the activating device, thereby releasing the contents of the chamber. It is also possible for the activating device to comprise a driving means which is operatively connected to the control module, for example this can be formed by an electromagnetic or electromechanically activated stamp which releases the contents of the depot on activation. Furthermore, it is an advantage if the blister is moved automatically by the activating device, for example by means of a stepping motor, in order to select automatically the next required reagent for release. In this way it can be ensured that the required reagent output is performed.

To ensure that the sequence of the sample output is adhered to it is possible that an activating element is assigned to each depot, wherein the activating elements are provided with an expiry mark. This can be provided for example by a color marking in the form of a traffic light system, with regard to a disposable sample delivery device a mechanical locking or unlocking device can also be provided so that the operator has to deliver the reagents in the correct order.

For the security of the application it is also an advantage if the control module is operatively connected with an outlet device of the sample delivery device, as in this way a targeted delivery of the sample chemical onto the sample carrier is possible, in particular onto the delivery section or possibly into the microfluidic system. As when performing the measurement expiry dates also need to be taken into account, the control module can also be configured so that the sample chemical is delivered from the sample delivery device into the delivery section of the sample carrier in a specific, time sequence. The outlet device can be formed by a controllable valve, for example a magnet valve, or a pulse-controlled delivery device similar to that of an inkjet printer, in a further development the throughput through the outlet device can be adjusted specifically or through a delivery opening with a variable diameter.

The previous developments have the advantage in particular that the operating safety is increased, in that a sequence and also a time sequence is adhered to reliably, wherein in particular it is the case that this delivery can be performed with a closed cover cap, i.e. in that the light-proof sealing of the sample carrier is also ensured during the addition of the sample chemical. The cover cap or the measuring device can comprise activating elements accessible from the outside in order to operate the sample delivery device accordingly.

In a further development it is possible that the depot is arranged pivotably underneath the activating element. For example, the depot can be a circular blister, which is placed in the delivery device and is pivoted step-by-step so that the required sequence of reagent delivery can be adhered to. In addition, the delivery device or depot can have a directing structure which defines a starting point and the direction of rotation. This can be formed for example by a starting nub and a sawtooth-like structure. Also a strip-like design of the depot is possible, whereby here too a starting position and the direction of progression can be determined.

After placing the sample carrier into the mounting device for example the microfluidic system can be filled with a preparative sample chemical in order to prepare the test sections for the subsequent measurement. In addition, it is an advantage if the sample carrier is already inserted into the mounting device and in particular the cover cap is closed, so that according to a further development the cover cap has a supply section which contacts the delivery section of the sample carrier. In this way it is possible to supply the sample chemical or the sample to be analyzed from the outside without having to handle the inserted sample carrier. As the chemical reaction can take place very soon after the addition of the sample to the analyzed, it is important if after delivering the sample the sample carrier is made light-proof, wherein on delivery to the sample carrier with an open cover cap here there is always a risk of incorrect operation, that the sample will be delivered and the cap is not closed in good time so that the measurement may be incorrect. With regard to single use also the supply section can be configured as a disposable device and after performing the measurement can be disposed of together with the sample carrier.

As on the sample carrier an identification or identity mark can be arranged according to a further development a non-contacting reading device can be provided on the measuring device. Said reading device can be in the form for example of an optical 1D or 2D-detecting sensor or a RFID transmission and receiving unit.

In order to reduce the thickness of the air gap and thereby ensure a better coupling of the sample carrier to the photosensitive sensor, according to further development a pressure means is arranged in the cover cap for exerting a force on the sample carrier. This can be in the form for example of an elastic material, which exerts a force on the carrier layer and thereby presses the sample layer on the cover layer of the photosensitive sensor. The elastic material can be formed for example by a foam material or by a spring-activated pretensioning element.

For a better understanding of the invention the latter is explained in more detail with reference to the following figures.

In a much simplified schematic representation:

FIG. 1 *a*) shows a cross-sectional representation of the measuring arrangement according to the invention having a sample layer and a cover layer;

*b*) shows a cross-sectional representation of the measuring arrangement according to the invention having fiber-optic panels with a tight Pack of optical fibers arranged next to one another in a row;

*c*) shows a cross-sectional representation of the measuring arrangement according to the invention wherein the light outlet side has a light deflecting structure;

d) shows a cross-sectional representation of the measuring arrangement according to the invention having an immersion layer applied onto the light outlet side and the cover layer;

FIG. 2 a) shows a representation of the signal distribution of a test section on the photosensitive sensor;

b) shows the measured dependency of the signal width on the photosensitive sensor, as a function of the distance between the test section and photodetector;

FIG. 4 shows a representation of the intensity distribution on the photodetectors as a function of the center-to-center distance of the test sections;

Figure 3:
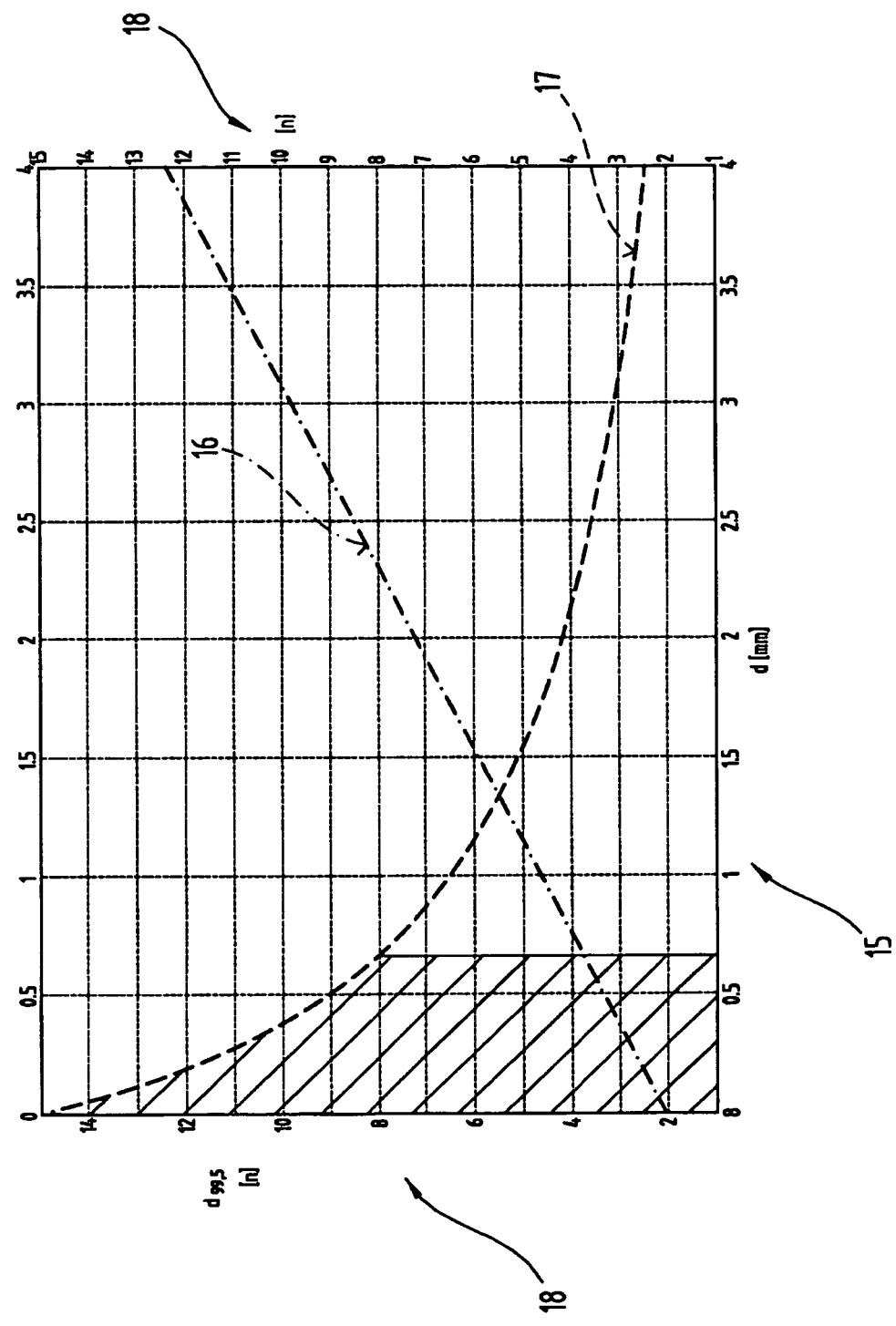
FIG. 3 shows the number of illuminated photodetectors as a function of the distance between the test section and photodetector.

FIG. 6 a) shows a representation of a configuration of the measuring device according to the invention;

b) and c) shows a further possible configuration of the measuring device according to the invention.

First of all, it should be noted that in the variously described exemplary embodiments the same parts have been given the same reference numerals and the same component names, whereby the disclosures contained throughout the entire description can be applied to the same parts with the same reference numerals and same component names. Also details relating to position used in the description, such as e.g. top, bottom, side etc. relate to the currently described and represented figure and in case of a change in position should be adjusted to the new position. Furthermore, also individual features or combinations of features from the various exemplary embodiments shown and described can represent in themselves independent or inventive solutions.

All of the details relating to value ranges in the present description are defined such that the latter include any and all part ranges, e.g. a range of 1 to 10 means that all part ranges, starting from the lower limit of 1 to the upper limit 10 are included, i.e. the whole part range beginning with a lower limit of 1 or above and ending at an upper limit of 10 or less, e.g. 1 to 1.7, or 3.2 to 8.1 or 5.5 to 10.

FIG. 1 shows a cross section of a measuring arrangement according to the invention, in which the dimensions have not been shown to scale to illustrate the essential features of the invention. In particular, the layer thicknesses and geometric configurations are not to scale.

The measuring arrangement 1 according to the invention comprises a sample carrier 2 with a carrier layer 3 and a sample layer 4. Furthermore, a photosensitive sensor 5 is provided which comprises a plurality of photodetectors 6, over which a transparent cover layer 7 is arranged. On an analysis side 8 of the sample layer 4 a plurality of test sections 9 are arranged spaced apart from one another, wherein the sample layer 4 with the analysis side 8 is arranged on the carrier layer 3 such that the test sections 9 are turned to face a volume of the microfluidic system 10, in particular the latter are arranged in the channel 23.

By means of the reaction of the sample material transported in the microfluidic system 10 with the reagents in the respective test section 9, in the test sections 9 there is a change in the optical property or a light emission based on chemiluminescence, so that the photodetectors assigned to the respective test section will detect a change in the incidental light intensity. The advantage of the invention is now that the distance 11 between the test sections 9 and the photodetectors 6 is less than 700 μm. According to the invention this is achieved for example in that the thickness 12 of the cover layer 7 is less than 500 μm and also the thickness 13 of the sample layer 4 is less than 200 μm.

At the transition from the light outlet side 14 of the sample layer 4 to the cover layer 7 of the photosensitive sensor 5 refraction and scattering effects may occur, which has the effect that the radiation characteristic of light coming from the test section corresponds virtually to that of a point light source. Therefore, the light of a test section 9 falls not only on a photodetector 6 arranged directly underneath but there is an expansion, whereby a portion of radiation reaches the assigned photodetector adjacent to the assigned photodetectors. By means of the configuration according to the invention of the distance 11 between the test sections 9 and the photodetectors 6 it is ensured however that the main portion of the radiation intensity only reaches one photodetector, the majority of the radiation intensity reaches a maximum of three photodetectors.

As the brightness signals to be detected are often only very small and thus are possibly covered by the unavoidable internal noise of each individual photodetector, it is particularly important if the largest possible proportion of the radiation intensity coming from a test section falls on an individual photodetector or that the total emerging radiation intensity remains restricted to the lowest possible number of photodetectors. Only in this way is it possible to achieve the greatest possible signal-to-noise ratio or a smaller lower detection limit. As the carrier layer 3 is mostly transparent, the boundary surface 43 of the channel 23 opposite the test sections 9 can be configured to be optically reflective for example. However, it is also possible that the carrier layer 3 itself is configured to be optically reflective.

During investigations which led to the invention it was established that the signal distribution or the signal width on the photosensitive sensor shows how many strips can be detected on a photosensitive sensor with a dynamic range of >100, i.e. a crosstalk of less than 1%. The most important parameter is the distance of the test section to the photodetector, because the signal width is directly proportional to this distance. The purpose of the measurements was to get an overview of the distribution of the light signal from the test sections printed for example by means of a capillary printing method.

From the measurement a Gaussian distribution of the signal on the photosensitive sensor was obtained. A characteristic variable for a Gaussian curve is the 1/e width, which is here denoted by c. Such signals are located within a width of $2*c$ 84.2% of the signal. 99.5% of the signal of a printed test section is distributed on a width on the photosensitive sensor of $4*c$. FIG. 2a shows the typical signal distribution of a test configuration according to the invention of a sample carrier with a printed test section (2×1 min) on a 190 μm thick sample layer over a photosensitive sensor, wherein the distance of the test section from the photodetectors is 1.54 mm. In this case 99.5% of the signal is within $4*c=6.03$ pixel. In this way it is possible to estimate that with this configuration a maximum of 4-5 different strips can be detected with an acceptable crosstalk and dynamic area.

Measurements were carried out at a distance of 1.3, 1.5, 2.5 and 3.5 mm between test section photodetector. If the average width (3 measurement values) of the detected signal (99.5% i.e. $4*c$) is applied to the photosensitive sensor against the distance between the test section and sensor, the relationship shown in FIG. 2b is obtained. If the brightness signal of a 1 mm wide test section is detected at a distance of 1.5 mm (0.19 mm film+1.35 mm glass to photosensitive area (according to the specifications of the sensor manufacturer)) thus 99.5% of the signal is distributed onto 6 pixel.

In this case the test sections would have to be printed at least 6 pixel=6 mm apart. In the preferred channel structure on a standard laboratory carrier (1"/3") with a channel length of 30 mm a maximum of 5 strips could be detected when at least one dynamic area of 100 (i.e. a crosstalk <1%) is to be covered.

By means of this method the possible number of detected test sections can be determined, as a result of these investigations the dependencies shown in FIG. 3 are obtained. Over the distance 15 between the test section and the photodetector two curves are entered, a virtually linear curve 16 and an essentially exponential curve 17 resulting from this curve. The virtually linear curve 16 shows the dependency at which distance 15 between a test section and the photosensitive sensor 99.5% of the total intensity of light coming from the test section falls on what number 18 of photodetectors. It can be seen from this diagram for example that at a distance of 1 mm between the test section and photodetector, 99.5% of the total intensity reaches almost 5 photodetectors. If the channel length is divided (i.e. 30 mm) by the 99.5% width (in mm) of the brightness signal of an individual test section, the second curve 17 is obtained. This curve shows the maximum of how many test sections 18 are possible at what distance 15 between the test section and sensor.

On the basis of the preferred channel length of 30 mm the desired measurement result was optimized such that at least eight test sections can be detected and evaluated by means of the detecting device according to the invention. The cross-hatched area shows below what distance from test section to photodetector more than 8 strips can be detected. From the diagram for eight strips, by analysis of the curve 17, a value of about 0.7 mm is obtained.

FIG. 4 shows the so-called signal crosstalk, i.e. how heavily the brightness signal acts owing to its intensity distribution from a test section onto the adjacent photodetectors. In particular, here the distance 19 between the test sections 9 is important, as the greater this distance 19, the fewer signal portions of a test section fall in the detection area of the respectively adjacent test sections and thereby of the assigned photodetectors—assuming a constant distance between the test section and photodetector. FIGS. 4a and 4b in the lower diagram shows respectively the situation in which each test section 9 emits a maximum brightness signal, wherein the usual intensity distribution of the brightness signal is shown by dashed lines. In FIG. 4a the distance 19 between the individual test sections is 3 mm, in FIG. 4b this distance is 4 mm, so that here only very small portions of the radiation intensity of a test section act on adjacent test sections. A low crosstalk is particularly important if with two adjacent test sections there are very different intensity reactions, so that the brightness signals are very different. The boundary area is formed in that on a test section the maximum brightness reaction takes place, on the adjacent test section the smallest possible detectable sample reaction takes place. By means of the configuration according to the invention with a distance of less than 700 µm between the test section and photodetector it is also ensured in this case, that the brightness product of the intensive reaction does not overlay that of the very weak reaction and thus a clear separation of the two reaction products is possible.

A large distance between the test sections has the additional advantage that in this way also imprecisions which occur when applying the test sections onto the sample layer, for example by printing, and imprecisions which occur during the insertion of the sample carrier into the mounting device, have no or only very little affect on the detecting values, in particular on the signal-to-noise ratio, on the lower detection limit value and crosstalk. In particular, with this configuration at a determined concentration value a standard deviation of 1.5% is achieved, whereby the concentration value is practically independent of the precise positioning of the test sections or the arrangement in the mounting device. This configuration has the particular advantage that untrained staff are also able to use it, as errors in the alignment will not affect the measurement results significantly.

Figure 5:
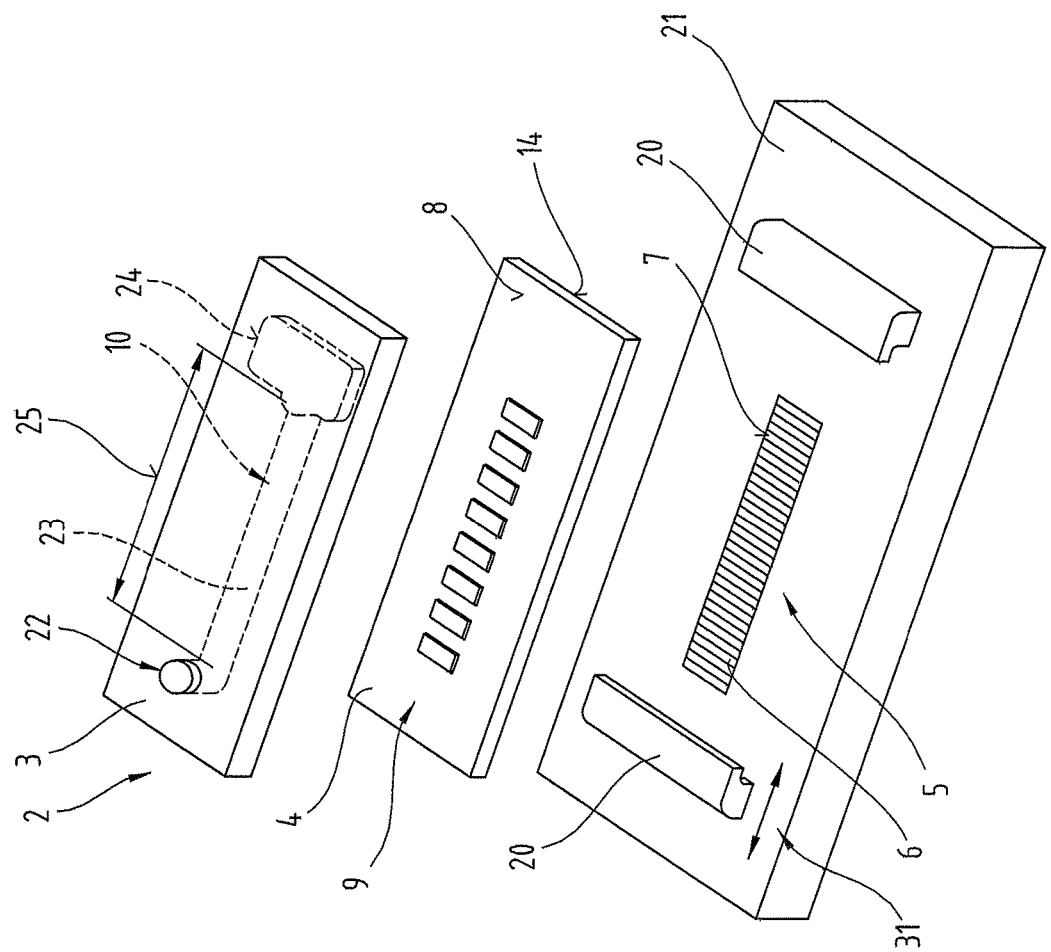
FIG. 5 shows an exploded view of the measuring arrangement according to the invention.

FIG. 5 shows an exploded view of the measuring arrangement 1 according to the invention comprising the sample carrier 2 with the carrier layer 3 and the sample layer 4. The sample carrier 2 is arranged detachably in a mounting device 20, so that the light outlet side 14 of the sample layer is arranged facing the photosensitive sensor 5. The photosensitive sensor 5 is arranged in turn in a base body 21, wherein the individual photodetectors 6 are covered by a transparent cover layer 7. On the analysis side 8 of the sample layer 4 a plurality of test sections 9 are arranged. The sample layer 4 is arranged in turn on the carrier layer, so that the test sections 9 face a volume of the microfluidic system 10, wherein when delivering a sample to be analyzed to the delivery section 22, because of the geometric characteristic of the channel 23, there is a capillary movement of the analyte from the delivery section 22 through the channel 23 to a reservoir 24. In this way there is also contact of the analyte with the test sections 9, whereby in the respective test section, in the presence of a corresponding analyte in the sample, a chemical binding reaction takes place, which leads to a change in the spectral properties or a chemiluminescent light emission. With a channel length 25 of 30 mm for a standard-1"/3" sample carrier 2 the measuring arrangement according to the invention was optimized such that eight test sections 9 of a total 32 of individual photodetectors 6 of the photosensitive sensor 5 are detected so that 99.5% of the brightness signal assigned to the test section is detected by three photodetectors 6 respectively.

The mounting device 20 is configured for example such that the sample carrier 2 is placed in a fixed part of the mounting device and is kept fixed by a second, movable and/or foldable part of the mounting device. It is also possible that in part of the mounting device a pretensioned element is arranged which is compressed on inserting the sample carrier and thus fixes the sample carrier in the mounting device.

Figure 6A:
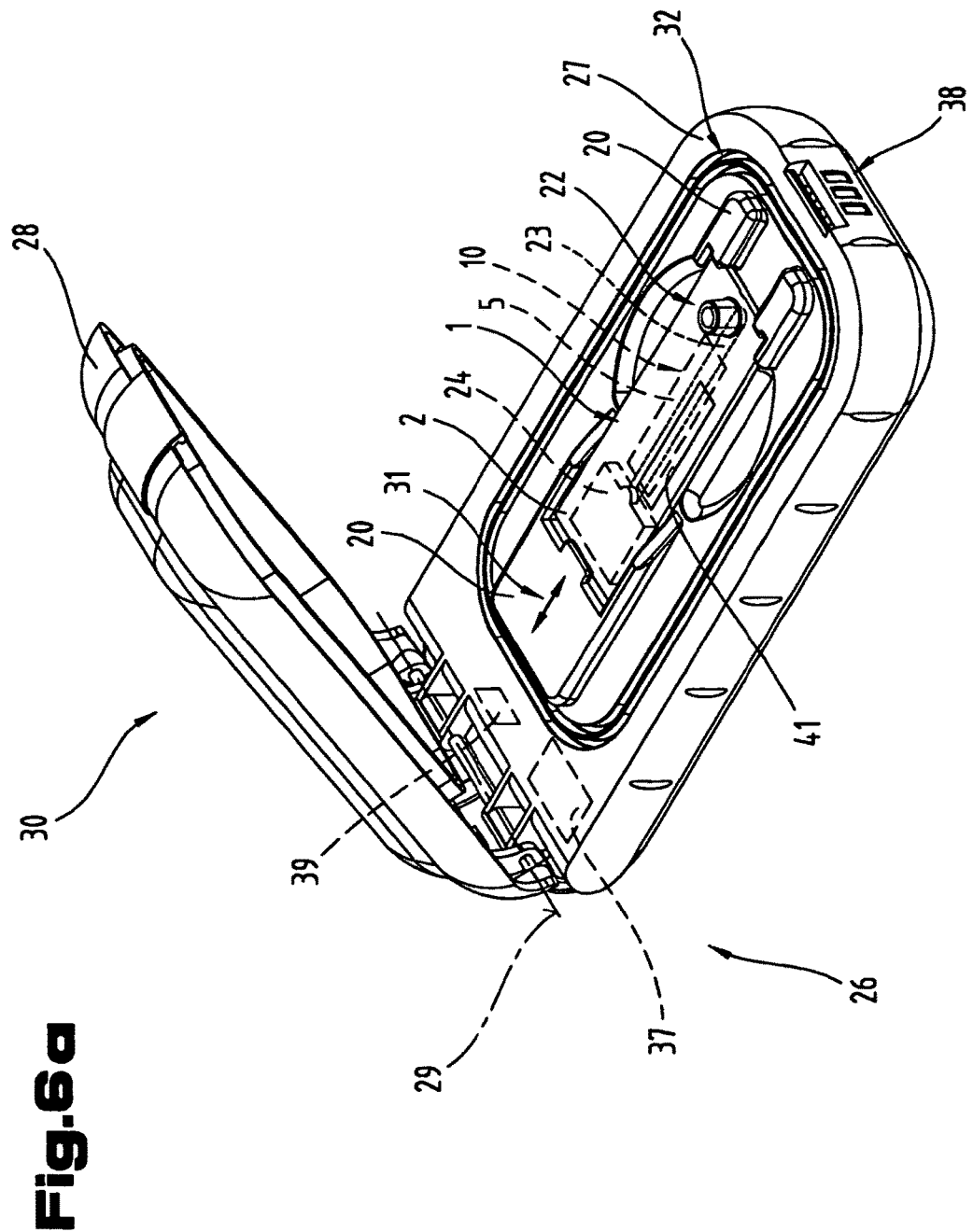

FIG. 6a shows a measuring device 26 according to the invention, comprising a measuring arrangement 1 in a base body 27, wherein a cover cap 28 is arranged pivotably about a pivot axis 29 between a measuring position and a supply and removal position 30.

The photosensitive sensor 5 of the measuring arrangement 1 is preferably arranged in the base body 27, preferably such that the sample carrier 2 is held in the mounting device 20 such that the test sections are arranged along the channel 23 with their light outlet side over the photodetectors of the photosensitive sensor 5. The mounting device 20 can for example comprise a fixed and a longitudinally displaceable, spring-tensioned holding part so that on inserting the sample carrier 2 the movable part can be moved in longitudinal direction 31, in order to facilitate the insertion of the sample carrier and fixes the latter accordingly after springing back into the holding position. In addition to a longitudinally displaceable configuration also a folding or snapping mechanism can be provided. It is also possible that in at least one of the holding parts a pressure means is provided, for example a rubber or spring element, which as described above fixes the sample carrier after insertion.

If the cover cap 28 is pivoted into the measuring position by means of a sealing element 32 the inner chamber, in particular the sample carrier 2 and the photosensitive sensor 5, is closed to be impermeable to light from the environment. The sealing element 32 can be formed for example by a tongue-and-groove connection, in the base body 27 in addition a peripheral groove-like depression can be provided, in which a correspondingly opposite spring of the cover cap 28, on pivoting the latter into the measuring position, engages and closes the inner chamber to make it impermeable to light. The sealing element 32 can however also be formed by an elastically deformable element, for example a foam material or a rubber seal, whereby in turn on closing the cover cap 28, on the basis of a compression of the sealing element 32, a light-proof closure of the inner chamber of the measuring device from the environment is achieved. The sample carrier 2 comprises a delivery section 22, in which the sample to be analyzed is deposited, which is moved because of the dimensioning of the channel 23 of the microfluidic system 10 automatically from the delivery section 22 to the reservoir 24. The delivery of sample material onto the delivery section 22 is problematic however in that on the one hand the amount to be delivered has to be adhered to precisely as far as possible or a sequence of the delivery of the sample chemical. Furthermore, after the delivery of the sample material by guiding the latter past a reaction occurs on the test sections and thereby there is a change in the optical properties or light emission in the test sections. If at this moment the cover cap 28 is not yet in the measuring position this can lead to inaccurate measurements.

Figure 6B:
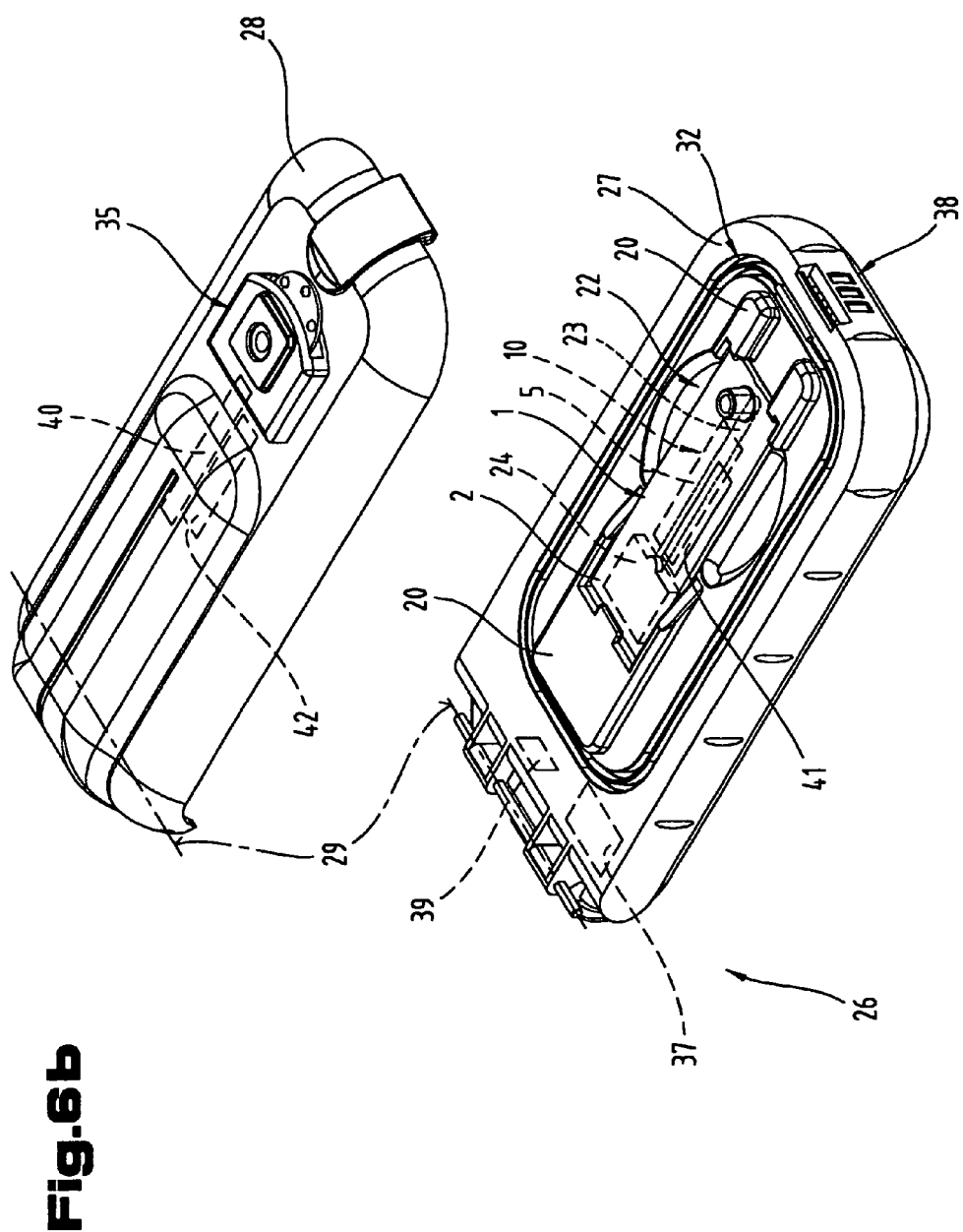
Figure 6C:
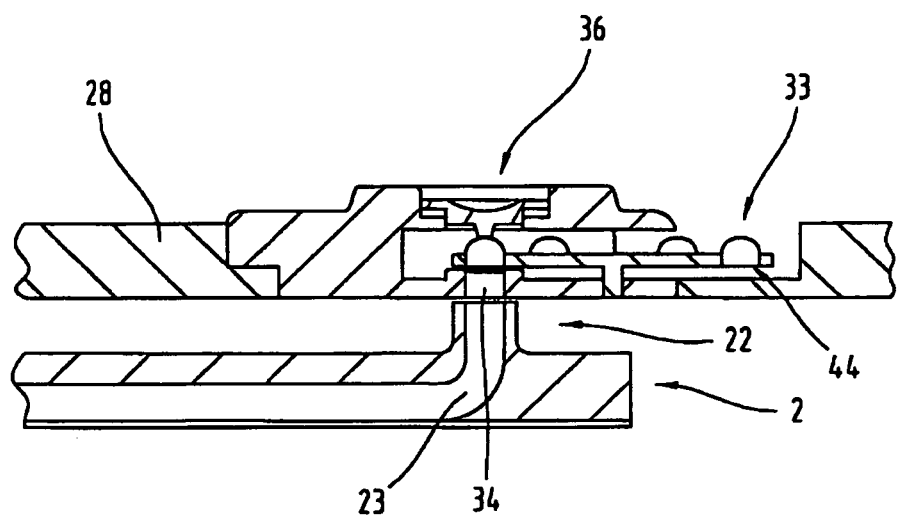

FIGS. 6b and 6c show a further possible configuration of the measuring device according to the invention, in which for example in the cover cap a supply device 34 can be provided which contacts the delivery section 22 for the fluid-tight delivery of the sample material and also ensures the light-proof sealing of the sample carrier 2 from the environment. Thus the sample carrier can be inserted into the mounting device 20 and then the cover cap 28 can be closed without sample material or sample chemicals being already located in the microfluidic system 10, whereby it is ensured that no chemical reaction is triggered in the test sections. Only then, with a closed cover cap and reliable formation of a light-proof seal of the sample carrier, are the reagents or the sample to be analyzed delivered to the supply device and conveyed from the latter to the delivery section 22 of the sample carrier 2. As further reagents may be necessary to perform the sample analysis the measuring device 26 can also comprise a delivery device 35 for reagents. The delivery device 35 comprises preferably an activating element 36 and connectably replaceable depot 33, which is configured for example as a blister and comprises a plurality of closed containers in which reagents are arranged. After activating an activating element 36, in the case of having a blister as the depot 33, the seal 44 of the reagent chamber is broken and the reagent is transferred via the supply device 34 into the delivery section 22 and thereby into the microfluidic system 10.

To ensure the sequence of the sample delivery a plurality of activating elements 36 can be provided for example which have an expiry mark, for example in the form of a numbering or colored code, for example a kind of traffic light system. In this way it is ensured that the sample delivery is performed with a closed cover cap and thus a light-proof sample carrier and that the reagents can be delivered to the sample to be analyzed in the correct sequence, in the predefined amount and in particular with a closed cover cap. The depot can also specify an activating direction, for example in that the depot is mounted rotatably in the discharge device and after the delivery of the reagent is rotated further manually or automatically. An automatic activation can be formed by a mechanical locking or snapping device which engages in a suitably configured counter point of the depot. According to one development the control module is in operative connection with the activating elements, and thus delivers the reagents automatically and in the correct sequence. In addition, also a locking element 38 can be formed with a contacting device, whereby the closing of the cover cap 28 triggers the measuring procedure. At the end of the measurement for example the locking element 38 can be controlled by the control module 37, so that a mechanical locking device is deactivated and the cover cap 28 pivots automatically into the supply and removal position 30.

In an advantageous development the supply device 34 can also be part of the depot 33, so that for the purpose of single use the supply device 34 together with the depot 33 and the reagents contained therein is replaced after each use so that a fresh, clean supply device 34 is always used for the measurement.

The control module 37 however is configured in particular to evaluate the individual photodetectors of the photosensitive sensor 5, in particular to evaluate the electrical signal proportional to the incidental brightness signal, process it accordingly and provide it to a communication connection 39. Said communication connection is preferably formed by a USB communication connection, but other wired or wireless communication connections from the field of data transmission are possible. For example, but not exclusively, it is possible to use: RS-232, RS-435, Bluetooth, zigBEE, IRDA or Firewire.

In addition to chemiluminescent measurements, in which because of the chemical binding reaction in the test section there is a light emission, the measuring device 26 according to the invention can also perform transmission measurements, in which in the test section because of the chemical reaction there is a change in the transmittance. In addition, the cover cap 28 comprises a lighting device 40, which is preferably controlled by the control module 37 and emits light with a specific wavelength or with a selectable or adjustable wavelength in the direction of the sample carrier 2. The light penetrates the test sections and is damped to varying degrees according to the chemical reaction which can be evaluated as the time path of the detected brightness signal.

The lighting device 40 can also be used in addition for calibrating the photosensitive sensor 5, in that before performing the measurement the photosensitive sensor is illuminated and the detected initial brightness value is saved as a calibration or zero point value. In this way manufacturing-related irregularities or contamination of the individual photodetectors of the photosensitive sensor can be offset, which is an advantage in particular during the detection of reactions on a plurality of test sections when the individual reactions are of varying strength so that possibly deviations form a significant part of the measurement result and thus the measurement result would be clearly distorted.

Furthermore, an identification mark 41 can be provided on the sample carrier, which is applied for example as a clear serial number or type information in the form of a 1- or 2-D-code. The identification mark 41 can also comprise a data memory, for example in the form of a data-matrix-code, in which calibration data of the individual test sections or analysis relevant parameters are stored for example. The identification mark 41 is read by a reading device 42 of the measuring device 26, whereby the reading device 42 preferably communicates with the control module 37, which receives the calibration or identification data, parameterizes the measuring device accordingly and performs the measurement.

To ensure accurate repeatability and to be able to offset deviations caused during production, it is an advantage that prior to the delivery of the sample to the sample carrier the lighting device is activated and a calibration of the photosensitive sensor is performed. By activating the lighting device all of the photodetectors of the sensor are charged by an even brightness signal, or with a known brightness distribution, so that deviations from the desired brightness distribution can be interpreted as interference signals and the detected brightness signal can be corrected accordingly. In particular, during the production of the test sections there may be slight deviations in the reactivity of the applied sample chemistry or the individual photodetectors of the sensor can vary slightly in sensitivity. Also by means of the arrangement of the sample carrier in the mounting section there may be slight misalignment or contamination, whereby a systematic fault arises which without correction or calibration can significantly falsify the detected concentration values. Said calibration can be performed only for the photodetectors, i.e. with a closed cover cap, without an inserted sample carrier, but also a calibration of the whole system is possible, i.e. when the sample carrier is inserted but no sample or reagent has been applied.

The exemplary embodiments show possible embodiment variants of the measuring arrangement and the measuring device, whereby it should be noted at this point that the invention is not restricted to the embodiment variants shown in particular, but rather various different combinations of the individual embodiment variants are also possible and this variability, due to the teaching on technical procedure, lies within the ability of a person skilled in the art in this technical field. Thus all conceivable embodiment variants, which are made possible by combining individual details of the embodiment variants shown and described, are also covered by the scope of protection.

FIGS. 6b and 6c show a further and possibly independent embodiment of the measuring device, wherein the same reference numbers and component names are used as in the preceding figures. To avoid unnecessary repetition reference is made to the detailed description of the preceding figures.

Finally, as a point of formality, it should be noted that for a better understanding of the structure of the measuring arrangement or measuring device, the latter and its components have not been represented true to scale in part and/or have been enlarged and/or reduced in size.

The problem addressed by the independent solutions according to the invention can be taken from the description.

Mainly, the individual embodiments shown in FIGS. 1 to 7 can form the subject matter of independent solutions according to the invention. The objectives and solutions according to the invention relating thereto can be taken from the detailed descriptions of these figures.

List of Reference Numerals

| | |
|---|---|
| 1 | measuring arrangement |
| 2 | sample carrier |
| 3 | carrier layer |

-continued

List of Reference Numerals

| | |
|---|---|
| 4 | sample layer |
| 5 | photosensitive sensor |
| 6 | photodetector |
| 7 | cover layer |
| 8 | analysis layer |
| 9 | test section |
| 10 | microfluidic system |
| 11 | distance |
| 12 | thickness |
| 13 | thickness |
| 14 | light outlet side |
| 15 | distance |
| 16 | curve form |
| 17 | curve form |
| 18 | number of sample sections |
| 19 | distance |
| 20 | mounting device |
| 21 | base body |
| 22 | delivery section |
| 23 | channel |
| 24 | reservoir |
| 25 | length |
| 26 | measuring device |
| 27 | base body |
| 28 | cover cap |
| 29 | pivot axis |
| 30 | supply and removal position |
| 31 | longitudinal direction |
| 32 | sealing element |
| 33 | depot |
| 34 | supply device |
| 35 | discharge device for reagents |
| 36 | activating elements |
| 37 | control module |
| 38 | locking element |
| 39 | communication interface |
| 40 | lighting device |
| 41 | identification mark |
| 42 | reading device |
| 43 | boundary surface |
| 44 | seal |
| 45 | light deflecting structure |
| 46 | fiber-optic panel |
| 47 | immersion layer |

The invention claimed is:

1. A measuring arrangement for optically evaluating a chemical reaction quantitatively, comprising
a sample carrier having a transparent carrier layer and a sample layer,
a photosensitive sensor with a plurality of photodetectors on a carrier body and a transparent cover layer arranged over the photodetectors,
wherein the photosensitive sensor is arranged in a base body,
the carrier layer comprising a discharge section, a microfluidic system and a reservoir,
the discharge section being connected via the microfluidic system to the reservoir, and the microfluidic system comprising at least one channel,
the sample layer having an analysis side and opposite the analysis side a light outlet side, wherein on the analysis side spaced apart from one another in a longitudinal direction of the sample layer, a plurality of test sections are arranged, wherein each test section of the plurality of test sections comprises a reagent corresponding to an analyte in a sample material transported in the microfluidic system for producing the reaction, and each test section of the plurality of test sections is a single body which is connected to the sample layer and the sample layer is arranged with the analysis side on the carrier layer such that the test sections face a volume of the channel of the microfluidic system and the sample carrier being arranged detachably in a mounting device of the base body, so that the light outlet side faces the photosensitive sensor and the test sections are arranged above the photodetectors, wherein to evaluate a result of the reaction, which is directly connected to the quantitative presence of the analyte in the sample material, the photosensitive sensor is configured to capture the test section and evaluate the time-dependent behavior of a detected optical signal, wherein the cover layer and the sample layer are disposed between the test sections and the photodetectors, a thickness of the cover layer is less than 500 µm, and a thickness of the sample layer is less than 200 µm, such that a distance between the test sections and the photodetectors is less than 700 µm and at least 99.5% of the electromagnetic radiation coming from a test section and reaching the photosensitive sensor is incidental on three photodetectors, wherein the plurality of photodetectors comprises a first photodetector disposed directly underneath a first test section of the plurality of test sections, a second photodetector disposed directly underneath a second test section of the plurality of test sections, and at least three additional photodetectors disposed between the first photodetector and the second photodetector, the first test section being disposed adjacent the second test section, and wherein a center-to-center distance between the first test section and the second test section is greater than or equal to 3-times the center-to-center distance of adjacent photodetectors.

2. The measuring arrangement as claimed in claim 1, wherein the photosensitive sensor comprises at least 32 photodetectors.

3. The measuring arrangement as claimed in claim 1, wherein the space between two adjacent photodetectors is less than 150 µm.

4. The measuring arrangement as claimed in claim 1, wherein the photosensitive sensor comprises at least two rows of photodetectors arranged spaced apart from one another.

5. The measuring arrangement as claimed in claim 1, wherein the at least one channel of the microfluidic system arranged above the photodetector has a length of 30-50 mm, a width of 1-4 mm and a height of 10-200 µm.

6. The measuring arrangement as claimed in claim 1, further comprising a sample deposited on the discharge section in the at least one channel and a pressure gradient formed with a resulting capillary force in the direction of the reservoir.

7. The measuring arrangement as claimed in claim 1, wherein the cover layer of the photodetector has a transparency maximum in a spectral range of 400-600 nm.

8. The measuring arrangement as claimed in claim 1, wherein a boundary surface of the at least one channel, which boundary surface is arranged opposite the photosensitive sensor is optically reflective and/or the carrier layer is optically reflective.

9. The measuring arrangement as claimed in claim 1, wherein the light outlet side has a light deflecting structure at least in some sections.

10. The measuring arrangement as claimed in claim 1, wherein the sample layer and/or the cover layer is in the form of a fiber-optic panel, as a tight pack of optical fibers arranged next to one another in a row.

11. The measuring arrangement as claimed in claim 1, wherein an immersion layer is applied onto the light outlet side or the cover layer.

12. The measuring arrangement as claimed in claim 1, wherein an identity or identification mark is arranged on the sample carrier.

13. The measuring arrangement as claimed in claim 1, wherein the sample layer and/or the carrier layer is configured as an optical polarizer.

14. A measuring arrangement for optically evaluating a chemical reaction quantitatively, comprising a sample carrier having a transparent carrier layer and a sample layer, a photosensitive sensor with a plurality of photodetectors on a carrier body and a transparent cover layer arranged over the photodetectors, wherein the photosensitive sensor is arranged in a base body, the carrier layer comprising a discharge section, a microfluidic system and a reservoir, the discharge section being connected via the microfluidic system to the reservoir, and the microfluidic system comprising at least one channel, the sample layer having an analysis side and opposite the analysis side a light outlet side, wherein on the analysis side spaced apart from one another in a longitudinal direction of the sample layer, a plurality of test sections are arranged, wherein each test section of the plurality of test sections comprises a reagent corresponding to an analyte in a sample material transported in the microfluidic system for producing the reaction, and each test section of the plurality of test sections is a single body which is connected to the sample layer and the sample layer is arranged with the analysis side on the carrier layer such that the test sections face a volume of the channel of the microfluidic system and the sample carrier being arranged detachably in a mounting device of the base body, so that the light outlet side faces the photosensitive sensor and the test sections are arranged above the photodetectors, wherein to evaluate a result of the reaction, which is directly connected to the quantitative presence of the analyte in the sample material, the photosensitive sensor is configured to capture the test section and evaluate the time-dependent behavior of a detected optical signal, wherein the cover layer and the sample layer are disposed between the test sections and the photodetectors, a thickness of the cover layer is less than 500 µm, and a thickness of the sample layer is less than 200 µm, such that a distance between the test sections and the photodetectors is less than 700 µm, wherein the plurality of photodetectors comprises a first photodetector disposed directly underneath a first test section of the plurality of test sections, a second photodetector disposed directly underneath a second test section of the plurality of test sections, and at least three additional photodetectors disposed between the first photodetector and the second photodetector, the first test section being disposed adjacent the second test section, and wherein a center-to-center distance between the first test section and the second test section is greater than or equal to 3-times the center-to-center distance of adjacent photodetectors.

* * * * *